United States Patent
Salbilla

(10) Patent No.: US 7,410,611 B2
(45) Date of Patent: Aug. 12, 2008

(54) IN-LINE METHOD AND APPARATUS TO PREVENT FOULING OF HEAT EXCHANGERS

(75) Inventor: Dennis L. Salbilla, 1411 Basswood Springs Ct., Houston, TX (US) 77062

(73) Assignee: Dennis L. Salbilla, Houston, TX (US)

( * ) Notice: Subject to any disclaimer, the term of this patent is extended or adjusted under 35 U.S.C. 154(b) by 626 days.

(21) Appl. No.: 09/773,438

(22) Filed: Jan. 31, 2001

(65) Prior Publication Data

US 2002/0102181 A1 Aug. 1, 2002

(51) Int. Cl.
- *A61L 2/00* (2006.01)
- *F28D 15/00* (2006.01)
- *F02D 7/00* (2006.01)
- *B08B 7/00* (2006.01)
- *B08B 9/00* (2006.01)
- *C02F 3/00* (2006.01)
- *H05B 3/58* (2006.01)

(52) U.S. Cl. .................. 422/22; 422/1; 165/5; 165/95; 165/303; 165/104.23; 122/379; 110/216; 134/1; 134/5; 134/19; 134/22.1; 134/22.11; 210/748; 210/243; 219/607; 219/618; 219/628; 219/643; 219/535; 204/158.2

(58) Field of Classification Search .............. 422/1, 422/22; 165/5, 95, 303, 104.23; 122/379; 110/216; 134/1, 5, 19, 22.1, 22.11; 210/748, 210/243; 219/607, 618, 628, 643, 535; 204/158.2, 204/164, 554

See application file for complete search history.

(56) References Cited

U.S. PATENT DOCUMENTS

| | | | | |
|---|---|---|---|---|
| 3,933,606 A | * | 1/1976 | Harms | 205/743 |
| 3,975,257 A | * | 8/1976 | Hulse | 204/665 |
| 4,370,236 A | * | 1/1983 | Ferguson | 210/634 |
| 4,505,758 A | * | 3/1985 | Carson | 134/1 |
| 4,885,139 A | | 12/1989 | Sparks et al. | |
| 4,892,139 A | * | 1/1990 | LaHaye et al. | 165/95 |
| 5,122,352 A | * | 6/1992 | Johnson | 423/243.12 |
| 5,318,102 A | | 6/1994 | Spokoyny et al. | |
| 5,846,301 A | * | 12/1998 | Johnson et al. | 96/52 |
| 6,089,023 A | | 7/2000 | Anderson et al. | |
| 6,451,210 B1 | * | 9/2002 | Sivavec et al. | 210/662 |

OTHER PUBLICATIONS

Oil and Gas Journal Aug. 10, 1998, pp. 78-79.
Oil and Gas Journal Jan. 11, 1999, pp. 40-44.

* cited by examiner

*Primary Examiner*—Jill Warden
*Assistant Examiner*—Monzer R Chorbaji
(74) *Attorney, Agent, or Firm*—Edmonds PC; Robb D. Edmonds

(57) ABSTRACT

The present invention relates to a method and apparatus for the prevention of fouling of process streams by the application of electric charge on process components. The electric charge may be attractive or repulsive to the foulants, they may be constant or variable and may be applied to any section of the process stream where convenient and wherein their preventive effects are optimized.

14 Claims, 8 Drawing Sheets

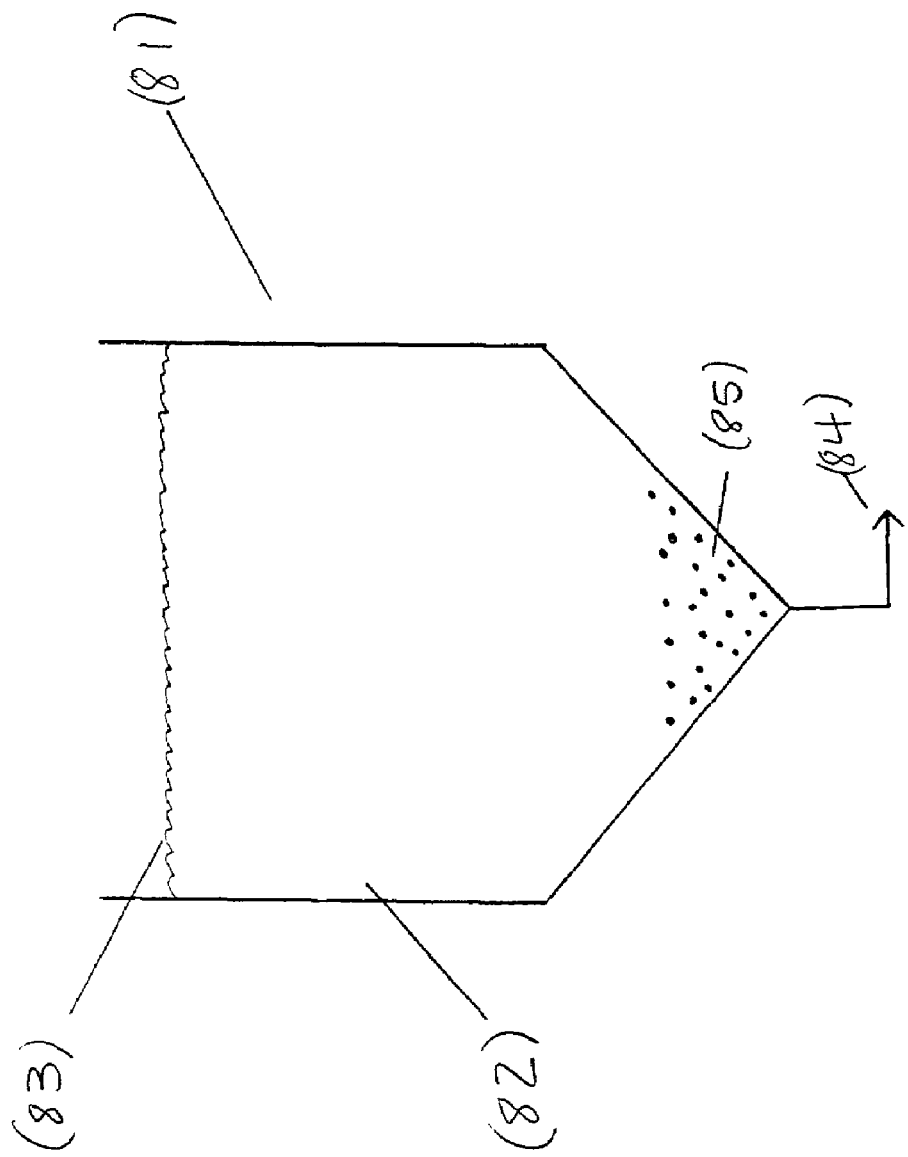

IN-LINE METHOD AND APPARATUS TO PREVENT FOULING OF HEAT EXCHANGERS

FIELD OF THE INVENTION

The present invention relates generally to an apparatus and process for the prevention of fouling of heat exchangers, especially fouling by coke, ash, and catalytic components in petroleum and petrochemical streams. Application of an electric charge is used to afford a means to prevent fouling and to avoid the resulting downtime required to purge and regenerate fouled equipment.

BACKGROUND OF THE INVENTION

In a number of industrial applications, it is either necessary or desirable to transfer heat from one fluid to another. This transfer is most commonly performed by a heat exchanger. Heat exchangers perform their function by using various flow designs and arrangements of different fluids, between which heat is transferred. These devices find use in refineries, fossil-fuel and nuclear power plants, in the chemical industry, air conditioning and refrigeration, as well as in cooling applications for small scale power devices. Oftentimes, they are given different names depending upon the environment in which they are used. Condensers, coolers, superheaters, evaporators, and other devices, are all properly considered heat exchangers.

One prominent application of heat exchangers is in distillation processes. These processes involve the separation of multi-component mixtures into purified fractions by one or more cycles of vaporization and condensation. Because the vaporized and condensed states are of different internal energies, heat transfer to and from these states is the most common means used for their interconversion.

In the petroleum industry, an interconversion method known as fractional or differential distillation is used. This technique is important for the separation of multi-component liquids in which the individual liquids have boiling points that lie close together. This technique involves repeated vaporization and condensation. Heat exchangers are of particular importance here. Due to the multi-component nature of the distillate and its multiple boiling points, the heat exchanger must be efficient enough to allow the closest possible thermal contact between the rising vapor and the descending condensate. Thus, efficient, trouble-free heat exchangers have particular applicability for use in connection with the refining of petroleum products and in the chemical and petrochemical industries.

Heat exchangers operate most efficiently where the surface area of the heat exchanger that is in contact with the medium to which heat is transferred is maximized. One way to achieve improved heat transfer is to minimize any contaminants located on the heat transfer surfaces. When heat exchange surfaces are deposited with particulates and other matter, thereby decreasing the effective area of the heat transfer surfaces, they are "fouled." Such fouling will adversely affect the heat exchange process and can potentially have a major negative impact on the economics of a refining operation. While minor fouling leads to a tolerable decrease in the efficiency of heat exchangers, this effect becomes more pronounced over time as the extent of fouling increases. In more extreme cases, fouling may lead to total failure of the heat exchanger with significant economic costs.

In petroleum refining applications, a common type of fouling is caused by particulate fouling. This may occur by the slow accumulation of foreign material, but is more likely to come from the breakdown of catalytic material used in the petroleum industry. Catalyst is often fabricated into small particles in which the active catalyst is immobilized onto a solid support with the goal of maximizing the catalyst surface area. Oftentimes, the catalyst is impregnated into the pores of a solid support. With time, the catalyst particles degrade and migrate into areas where they may foul equipment. The heat exchanger is one piece of equipment that is particularly susceptible to fouling due to the need to keep its surfaces contaminant-free. The small particle, high surface-area catalysts used in the refining industry are of the ideal configuration to cover the surface of the heat exchange element and decrease its efficiency. The most common scenario of particulate fouling by catalysts in petroleum refining is by the mechanisms of migration and attachment.

For example, Clarified Slurry Oil (CSO) heat exchangers are used in the field of petroleum refining in connection with fluid catalytic cracking units. They play an integral role in keeping the Fluid Catalytic Cracking Unit (FCCU) in heat balance and at maximum charge rate. The heat source of the main distillation column is the FCCU reactor effluent entering between the Light Cycle Oil (LCO) draw and the distillation tower bottom.

The CSO heat exchangers in a typical oil refining process are susceptible to fouling when the catalyst containment efficiency of the FCCU cyclone separators decreases. This event will usually occur near the end of run or when the integrity of the catalyst containment equipment is compromised. Fouling occurs when a layer of catalyst particles accumulates on the heat transfer surfaces of the heat exchanger. This layer of catalyst reduces the efficiency of the heat exchanger to transfer heat as a result of the loss of heat transfer surface area on the fouled surfaces.

One interim response to such a situation is to decrease the FCCU feed rate. This has the undesirable effect of decreasing product throughput.

The typical curative response to such a situation is to take the unit off-line and perform cleaning maintenance. While this will regenerate the apparatus to its earlier efficiencies, it is also an undesirable remedy. Whenever the FCCU is in turndown mode or is taken off-line for unscheduled maintenance, the refiner is losing the opportunity to operate the FCCU at its optimal revenue-generating capacity. Unplanned maintenance is much costlier than planned maintenance. Resources must be secured with little if any, lead time. The effect on unit operations costs of downstream units (e.g., wastewater treatment) will increase.

Moreover, cleaning the CSO heat exchangers is also a potentially dangerous task. A high pressure steam lance is typically used to remove the fouling layer. Liquid temperatures are approximately 700° F. The process is labor intensive and the liquids used have the potential to cause severe burns to personnel performing the operation. Any mechanism to eliminate or reduce the frequency of such maintenance will be beneficial to refining operations.

Because of the undesirable effects associated with fouled exchangers, there have been many attempts to address the problem.

For example, U.S. Pat. No. 4,370,236 teaches the purification of hydrocarbons by the electrostatic precipitation after the formation of an aqueous admixture of the hydrocarbon. The '236 purification method requires the precipitation of foulants. Additionally, the teaching of the '236 patent requires, among other things, the formation of an aqueous liquid.

In a somewhat related field, there have been efforts to address particulate fouling in gaseous streams. U.S. Pat. No. 5,318,102 to Spokoyny, et al., teaches how to improve resistance to fouling in heat exchangers for gas streams through the use of plate packs. Plate packs are a unique configuration of an array of heat transfer plates. This array affords a gradual decrease in pressure of the gas stream while maintaining good thermal contact with the gas and minimizing particulate deposition. This process only contemplates gaseous streams and fails to consider other fluids and, in particular, petroleum streams. U.S. Pat. No. 4,885,139 to Sparks, et al. also focuses on gaseous streams; in particular, on the removal of acidic gases from gaseous flow streams. Sparks also fails to consider fluids and requires a complex multistage process. Finally, U.S. Pat. No. 6,089,023 to Anderson et al. teaches a method that employs a decrease in temperature of the exhaust gas stream, thereby improving the efficiency of a subsequent electrostatic precipitation. Anderson, like Spokoyny and Sparks, is directed toward gaseous streams.

One common practice in the petroleum refining industry used to address the problem of foulants uses an arrangement of columns or chambers packed with ferrous metallic particles to which a charge is applied. The hydrocarbon fluid to be purified of contaminants is passed through the columns. While this method utilizes electric charge for purification, it is in actuality, a form of chromatography, as the contaminant particles are trapped by the column packing. The Gulftronics™ catalyst separator is currently the most common known commercial embodiment of this technology. It is a modular (skid mounted) apparatus designed to be placed in the CSO circulation loop. CSO enters the individual chambers of the Gulftronics™ which are aligned in series. Each chamber is filled with ferrous metallic spheres. An electronic charge is applied to these spheres to attract the catalyst particles to their surface, thus clarifying the CSO stream. Once the spheres accumulate enough catalyst particulates, the electric charge is turned off and the flow is redirected to new or regenerated purification chambers or back to the FCCU riser or to a slurry settler. When an adequate amount of time to purge the saturated chambers has elapsed, the flow may again be redirected to the original purification chambers which now contain reconditioned spheres. This method and apparatus entails complex hardware and requires intensive scheduled maintenance. The chromatographic columns must be regenerated or replaced as they become saturated. A non-chromatographic method which does not involve column regeneration or column switching is desirable. Moreover, space must be allocated for it immediately upstream of the CSO heat exchangers. Piping modifications must be made to tie the apparatus into the CSO circulation loop. Piping modifications must be made from the prior art apparatus into the FCCU riser or a slurry settler.

Because of the shortcomings of the prior art, the need presently exists for a simple in-line method to prevent or minimize fouling in these complex liquid streams.

SUMMARY OF THE INVENTION

It is therefore the object of this invention to provide a method and apparatus for the prevention of fouling of heat exchangers by contaminant accumulation. In a preferred embodiment, the method and apparatus prevents or minimizes fouling in complex liquid streams without the short coming of existing curative responses, interim measures, or complex apparatus.

In the generalized embodiment, the purification process involves applying an electric charge to an object within the flow path of the hydrocarbon stream to be purified, and adjusting the charge magnitude, as necessary to direct the movement of the contaminants. In a specific embodiment, the object to which such charge is applied is either upstream of the heat exchanger to be protected, or on the heat exchanger itself. In another embodiment, the object to which such charge is applied is a slurry settler. The electric charge is typically a constant electric charge.

In an alternative embodiment, the electric charge is modulated. In a specific embodiment using a modulated electric charge, the charge is sinusoidally modulated.

In the preferred embodiment, the process involves direct application of the electric charge to the heat exchanger. Preferably, this charge is applied to the chassis or shell of the heat exchanger, but may alternatively be applied to other parts of the heat exchanger, such as the baffles, or a floating head.

In another embodiment, the electric charge is applied to an auxiliary device located upstream of the heat exchanger in order to trap contaminants before their arrival at the heat exchanger. In this embodiment, the auxiliary device may be a vessel, a section of pipe, a spare heat exchanger, or other device. Alternatively, the charge may be applied immediately downstream of the heat exchanger. The charge magnitude must be optimized according to the distance from the surface to be protected; this is preferably done by measuring contaminant levels of the fluid in the area of the heat exchanger.

In the preferred embodiment, the electric charge is controlled via a feedback loop that responds to a feedback stimuli. Preferably, this feedback stimuli is related to the relative contaminant levels of the fluid stream in the vicinity of the heat exchanger. This purity may be determined by turbidity measurement or by any other analytical test. Preferably, this measurement may be made in-line and in real time resulting in a rapid feedback response; alternatively, the measurement may be made off-line with delayed feedback to control the electric charge.

In the preferred embodiment, a repulsive electric charge is used. In this mode, a repulsive charge to the heat exchanger itself in order to keep the heat exchanger free of contaminants.

Alternatively, an attractive charge may be used. If an attractive charge is used and if it is applied to the heat exchanger, it is preferably applied to a portion of the heat exchanger that will result in particle deposition on those parts of the exchanger which will not adversely affect its efficiency.

In another embodiment the invention is directed toward a distillation apparatus comprising a distillation column, a heat exchanger, and a voltage source. The distillation column and the heat exchanger are in thermal contact with one another.

BRIEF DESCRIPTION OF THE DRAWINGS

FIG. 8: Slurry Settler used to perform a gravity separation of solid particulates from the CSO product prior to going to storage.

DETAILED DESCRIPTION OF THE INVENTION

While the present invention has application in a multitude of industries using heat exchange on fluid flows, for illustrative purposes we focus herein on the field of petroleum refining. This focus should not be construed to limit the invention to any specific application. The present invention relates to both the processes and the apparatus' described herein.

As discussed above, heat exchangers perform a critical function in industrial processors. In particular, heat exchangers play a prominent role in petroleum distillation processes. When heat exchangers are fouled, efficiency is reduced. This efficiency can be reduced to the point at which a heat exchanger must be removed from service. Such a process is costly in terms of increased system downtime and labor costs.

Figure 1:
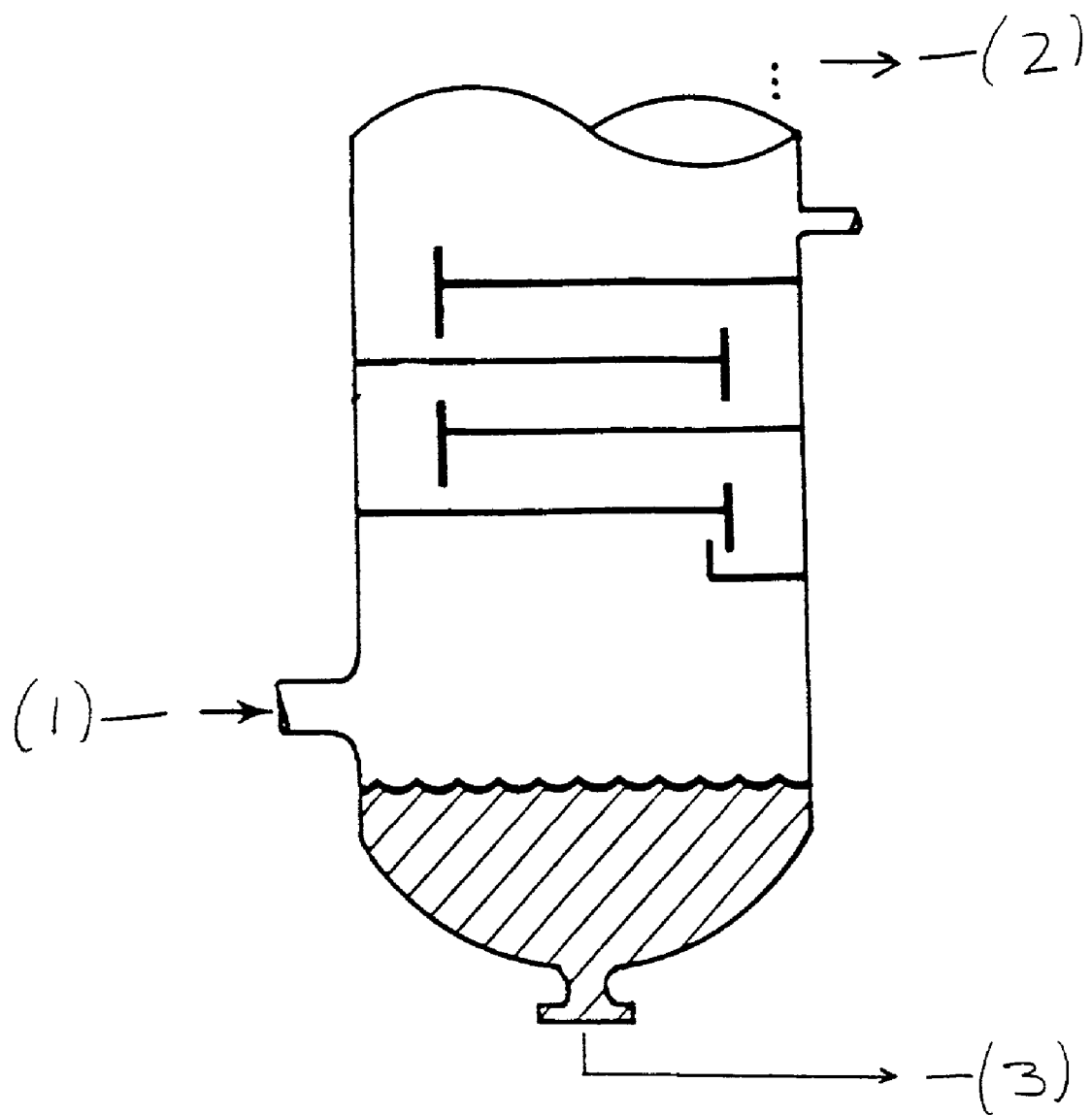
FIG. 1: Fluid Catalytic Cracking Unit and associated process components of a typical modern petroleum refining operation.

In particular, with reference to FIG. 1, the heat source (1) of the FCCU Main Column is the reactor effluent entering the tower between the LCO draw (2) and the tower bottoms draw (3). The temperature profile of the main column is determined by product cut point specifications and is highly dependent on the heat transfer efficiency of the heat exchangers especially the CSO heat exchangers. When heat exchanger fouling starts to effect the refiner's ability to maintain the desired temperature profile of the main column, a number of possible remedies are currently used to keep the FCCU from shutting down.

These adjustments and their associated consequences include:
1. Reducing feed rate to the FCCU reactor. Results in lost production capacity.
2. Increasing velocities through the CSO heat exchangers. Eventual decrease in FCCU feed rate.
3. Process a lighter (less carbonaceous) feed. Process/refinery economics are likely to be adversely effected.
4. Increase feed preheat temperature. Lower conversion decreases value of products.

The present invention affords the use of an electric charge as controlled by the applied voltage as a potential mechanism to avoid the aforementioned remedies, all of which have disadvantages associated with them.

The present invention provides an additional degree of freedom to operate the CSO heat exchangers. It affords greater ease and flexibility in the control of the tower's temperature profile during the later stages of the run when fouling typically becomes pronounced. It helps to maintain the CSO heat exchangers' heat transfer efficiency throughout the run. It enhances reliability by reducing or eliminating the need to perform cleaning of the CSO heat exchangers during runs. Its economic benefits include the maintenance of maximum FCCU charge rate as well as product throughput volumes and it makes optimum use of existing equipment without adding new hardware. Additionally, as fouling becomes pronounced, catalyst particulates are likely to become impurities in various petroleum products, thereby decreasing product quality. The present invention will reduce, and in some cases, eliminate this degradation in product quality.

The present invention addresses the need for efficient, simple apparatus and method for preventing the fouling of heat exchangers. In one aspect of the present invention, an electric charge is applied to a surface of a process element to be kept free of contaminants (i.e., the critical surface), or to a surface of an object near or upstream of the process element. The effect of the electric charge will be to trap contaminants or otherwise keep the process element or the critical parts of the process element free of contaminant. In a specific application, the process is petroleum refining, the process element is a heat exchanger and the potential contaminants are coke, fly ash and catalyst particles. In the process, the fluid stream consists of a hydrocarbon mixture. The critical surface in this specific application is the surface at which heat transfer occurs. The charge is ideally applied to a target surface at or upstream of the heat exchanger, but may be applied downstream of the heat exchanger so long as it is close enough and powerful enough to keep foulants away from the heat exchanger. Measurement of contaminant levels in the vicinity of the heat exchanger is one possible way to determine if the magnitude of the applied charge is sufficient. As contaminant levels increase, an increase in charge is called for. The charge may be attractive or repulsive. This charge is applied through the use of a voltage source electrically coupled (e.g., by a simple wire or other common means) to the target surface with electrically couplable connections and an electrical channel. The attractive or repulsive voltage can be direct (DC) or sinusoidal (AC). As long as the applied voltage and the resulting charge are of a sufficient magnitude to adequately attract or repel the foulants, it is immaterial whether the voltage is constant or modulated in some way (e.g., sinusoidally modulated). Either embodiment is useful in the present invention.

Fluid Catalytic Cracking Unit

Figure 2:
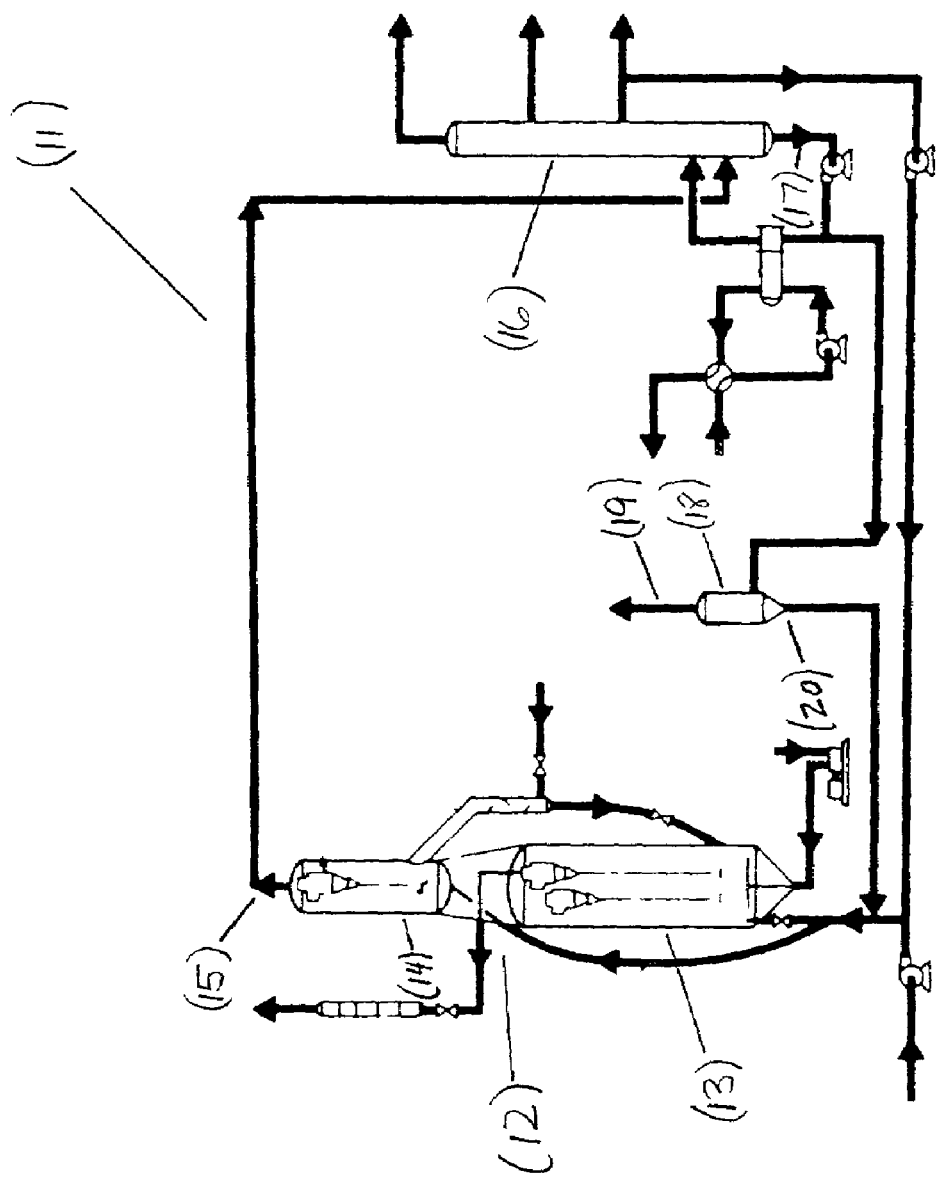
FIG. 2: Shell and Tube Heat Exchanger with electric potential applied to the internals. An attractive charge is applied to the inner surface of the shell. A repulsive charge is applied to the outer heat transfer surface area of the tube bundle. The charge is controlled remotely from the FCCU's central control room. The charge is adjustable to adapt to changing process conditions.

The present invention will now be explained in detail by reference to the FCCU. The FCCU is a vitally important unit within a modern high conversion refinery. It contributes the bulk of the gasoline to the refinery's gasoline pool, produces petrochemical feedstocks for downstream units, provides fuel gas used to produce steam in the boiler house, and makes a variety of other products such as kerosene, diesel, aviation fuel and bunker fuel. FIG. 2 illustrates the layout (11) of the cracking unit with the other immediately surrounding process elements of a modem petroleum refinery. The FCCU unit (12) consists of a Regenerator (13) and the Reactor (14). Output (15) from the FCCU is a mixture which has been enhanced in low molecular weight hydrocarbons through catalytic reaction. This output is sent to the main distillation column (16) to separate the various petroleum fractions by distillation. The column bottoms (17) are sent to a slurry settler (18) wherein the settler overheads (19) are the CSO product, the settler bottoms (20) are returned to the reactor for cracking, and the remainder of the settler bottoms are returned to the column. It is at this point, between the distillation column bottom and the return to the reactor that the CSO heat exchanger is located (not shown).

The CSO heat exchangers play an integral role in maintaining the proper heat balance of the FCCU Reactor and Regenerator. This proper balance allows the FCCU unit to run at optimal throughput loads. Maximum charge rate to the FCCU Reactor is highly dependent on the heat removal efficiency of the CSO heat exchangers. Most of the heat removed from the CSO is transferred to the FCCU feed. Warm feed temperatures of approximately 350° F. are necessary for a number of reasons. Most importantly, heat transferred from the CSO to the FCCU feed acts as major heat sink and warm feed reduces the amount of hot catalyst used to heat and vaporize the feed in the reactor riser. The refiner will typically increase CSO circulation before reducing feed rate on the FCCU to adjust the heat balance as fouling intensifies. This is an ongoing process as the efficiency of the heat exchangers is continually decreasing as the FCCU remains on-line. At some point, the refiner must shutdown the FCCU to perform required maintenance that includes cleaning the heat exchangers. With the present invention, the rate of circulation within the CSO heat exchanger may be maintained. If fouling intensifies, the applied voltage may be increased in order to increase the electric charge to preserve a contaminant-free status. Maintenance requirements will be minimized.

Applying an electric charge to the inner surface of the heat exchanger shell will attract the catalyst particles away from the heat transfer surface area of the tubes. Similarly, a repelling electric charge applied directly to the tube bundle will prevent the catalyst particles from depositing on the tube surface. Any suitable and commonly available voltage source is applicable in the present invention. As such, the voltage source may be one capable of supplying either a constant or modulated voltage.

Applying a strong electric charge on the inner surface or to the shell of CSO heat exchangers in a petroleum refining process is used to attract coke, ash and catalyst particles away from the critical surfaces (the heat exchanger tube bundles) which physically perform the transfer of heat. When the charge is applied to the critical surface of the heat exchanger, a repulsive charge is used to keep the surface contaminant-free. When the charge is applied to a target surface other than the critical surface, an attractive or repulsive charge may be used depending upon the proximity to the critical surfaces and the nature of the contaminant. Examples of process elements, other than heat exchangers which can have a charge so applied are vessels, pipes, slurry settlers, among other suitable process elements.

In the case of catalyst particles, the attraction (or repulsion) of the foulants is enhanced due to the amounts of ferrous metal contained in their composition. The charge may again be attractive or repulsive. Where it is applied directly to the critical elements, a repulsive charge is used to keep the elements contaminant-free. Converting from the attractive charge mode to the repulsive charge mode is accomplished by a reverse of polarity. Ideally, the voltage source should be variable to afford a ready response to changing conditions. Commonly available voltage sources are applicable to the invention. No other new equipment, major piping modifications, or additional space is required.

Temperature is a variable that is an inherent advantage to the present teaching. High process temperatures above 600° F. offer lower catalyst resistivities (see D. L. Salbilla, *Oil and Gas Journal*, Aug. 10, 1998, pg.78). High temperatures are part of the natural environment in the CSO heat exchangers of a typical petroleum refinery.

Application to a Heat Exchanger

Figure 3:
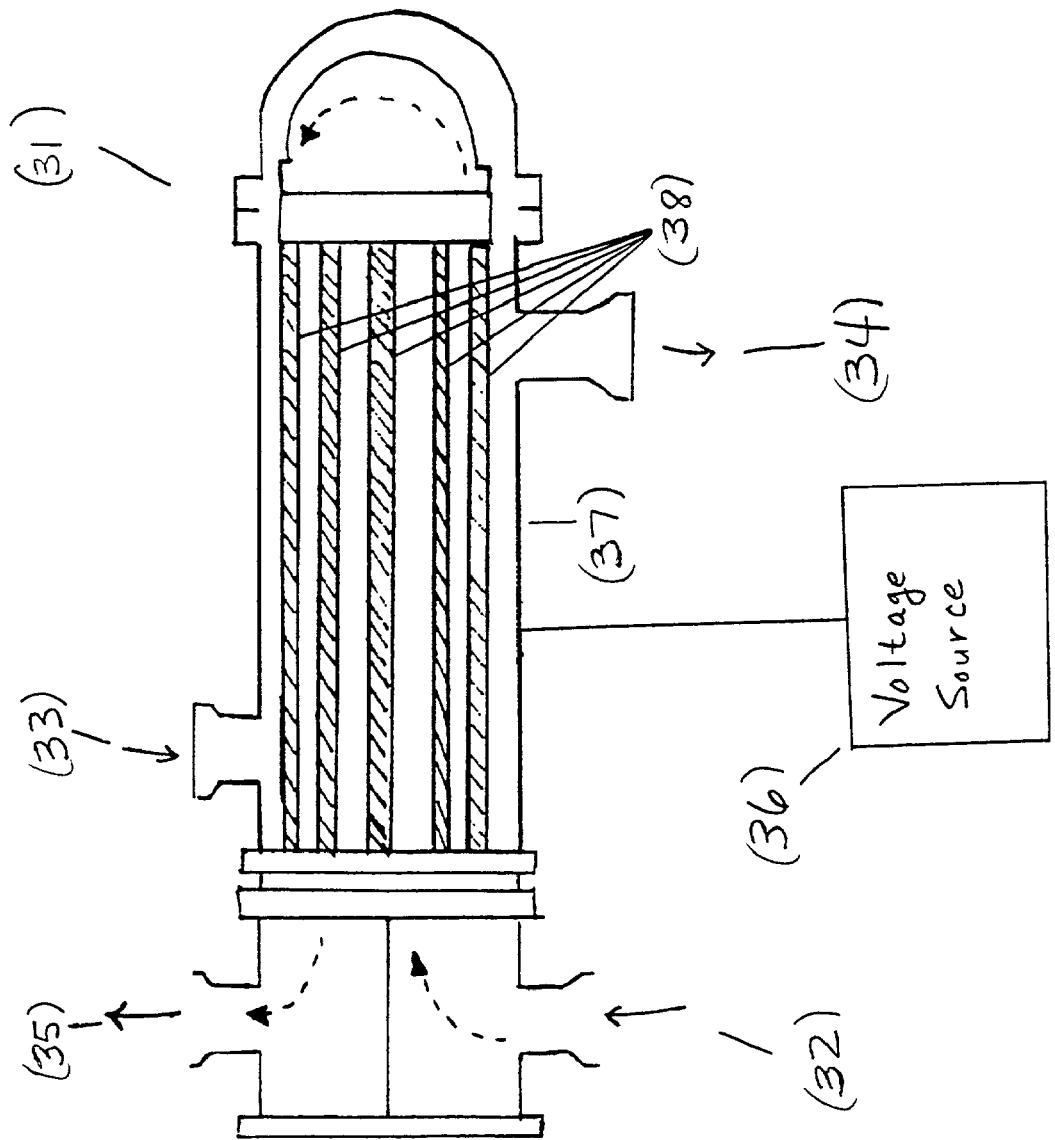
FIG. 3: Bottom section of main distillation column. FCCU reactor effluent enters the bottom section and is the heat source that drives the column's temperature profile. Clarified Slurry Oil is taken from the bottom of the column.

FIG. 3 demonstrates an embodiment of the present invention. In a typical CSO heat exchanger (31), cool feed (32) enters, undergoes heat exchange with hot CSO (33). Cool CSO (34) and heated feed (35) exits the unit. Preserving the heat transfer efficiency of heat exchanger (31) can be achieved by introducing a voltage from a suitable AC or DC voltage source (36) on the inner surface area of the shell (37) to attract the fouling particulate solids away from the exterior heat transfer surfaces of the tube bundle (38). Similarly, a repulsive charge can be applied to the tube bundle to deter fouling of the heat transfer surface. The voltage source may be connected by a variety of ways known to those skilled in the art. These connections may be made by welding, terminals, jumpers, or other means. By connecting the voltage source, a voltage may be applied to a preferred location.

The required charge magnitude used in these applications varies and is a function of ferrous metal content on the catalyst particles, temperature and CSO velocity through the heat exchanger. A FCCU operating cracking a clean gasoil and high catalyst replacement rate will have low metals levels detected on the catalyst. A residual oil cracking unit (RCCU) can be considerably metal-laden. Voltages are preferably strong enough to work with catalyst resistivities on the order of $1.00 \times 10^{13}$ Ω-cm. The voltage supplied may be manually set or, alternatively, it may be part of a feedback loop that adjusts the voltage in response to a signal indicative of fouling. As foulant levels within the fluid increase, the likelihood and extent of fouling will also increase. Increasing the magnitude of the applied voltage will enhance the anti-fouling effects. This is particularly useful during the end-of-run cycle wherein catalyst particles are more likely to migrate downstream. The feedback signal may be from turbidity measurements or from other analytical measurements which are indicative of the level of foulant in the stream adjacent to the heat exchanger tube bundle. Such analytical measurements may include, but are not limited to, spectroscopic, chromatographic, or electrochemical measurements quantifying the level of catalyst particles present in the sampled fluid. Alternatively, the signal could be a simple visual inspection of fluid. An external sampling loop may be used to draw a sample of fluid from the vicinity of the heat exchanger for either real time or off-line analysis. The results of the analysis are used to adjust the applied voltage. An increase in measured foulant dictates that the voltage should be increased such that foulant levels are returned to a normal range. This normal range is that level seen at the time of, or shortly after, the beginning of the run. The adjustments may or may not be automated. An example of an automated adjustment would be one which is computerized. For example, the turbidity or other analytical measurements may be automated, with results inputted into the computer. The computer would then adjust the voltage accordingly. Finally, in lieu of a turbidity or analytical measurement, the feedback signal may merely consist of the load on the heat exchanger necessary to maintain proper process conditions. As the load increases, foulant levels have increased and voltages changes are required.

Alternatively, conductivity or resistivity measurements may be used to determine contaminant levels which may then be used.

Heat Exchanger Configurations

Figure 4:
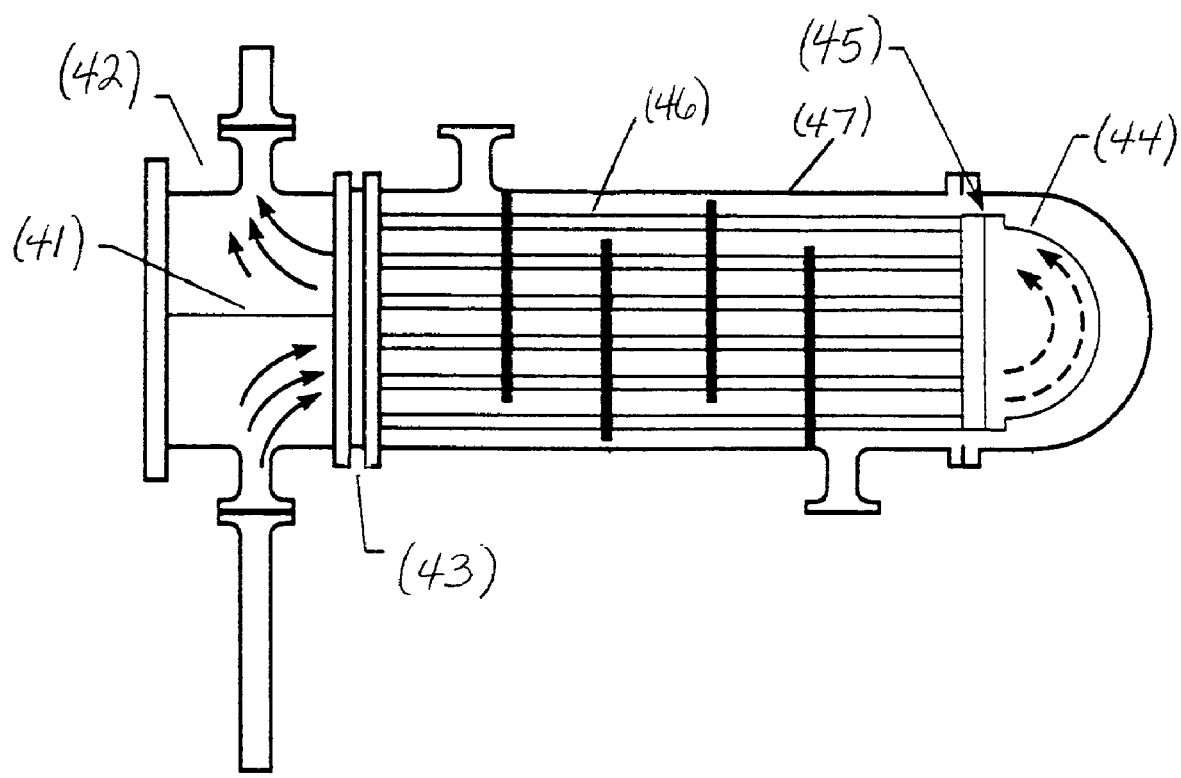
FIG. 4: Shell and Tube heat exchanger with a Floating Head
Figure 5:
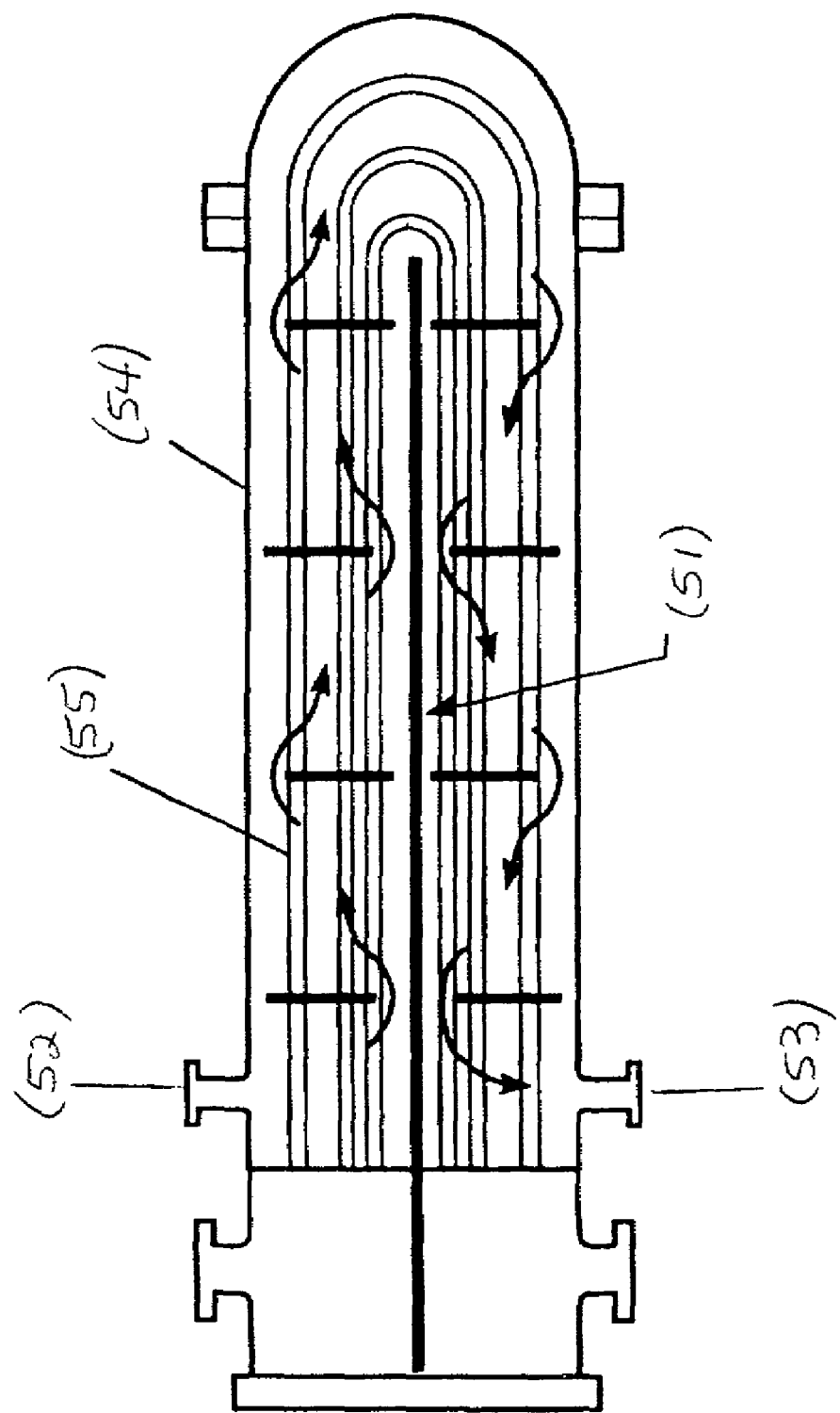
FIG. 5: Two Pass shell heat exchanger.
Figure 6:
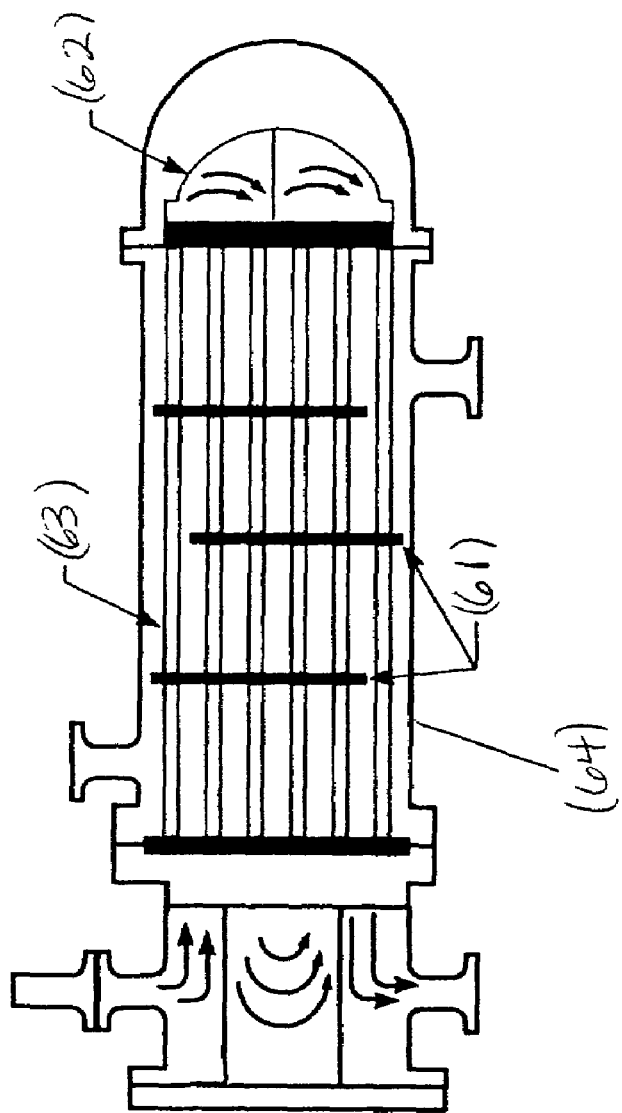
FIG. 6: Four Pass tube bundle heat exchanger with a Floating Head

Heat exchanger designs vary greatly due to application requirements, being for example, FIGS. 4-6 illustrate three alternative configurations. The present invention adaptable to each configuration.

In a typical refinery that operates a FCCU, the floating-head shell and tube heat exchanger design is popular (FIG. 4). In this design, a partition baffle (41) divides the channel head (42) into two sections. In this way, the fluid flow is directed through the channel head tubesheet (43) along the bottom tubes only. After traversing the length of the bottom tubes, the fluid enters the floating head (43) through the floating head tubesheet (44) where it makes a complete turn and flows along the top tubes. Notably in this design, the tubes are firmly attached to the channel head tubesheet (43) but float at the floating head tubesheet (44). This floating tubesheet design allows for the variable degree of thermal expansion that occurs between the tubes and the shell. This floating head is a convenient location to apply the remedial charge of this invention. Alternatively, a repulsive charge on the tubes (45) or the exchanger shell (46) is possible. Some shell and tube heat exchangers have individual U-bends in each tube in lieu of the floating head. In this design, each U-bends behaves as a floating head for each tube.

Different designs allow for multiple passes i.e., two-pass (FIG. 5) and four-pass service (FIG. 6) for maximum heat transfer. The notable feature of the two pass design is the longitudinal baffle (51) which directs an orderly flow from inlet (52) to outlet (53). This preserves an optimal thermal gradient along the flow path and prevents a "short-circuit" of the tube bundle. In this design, the charge application can be on the longitudinal baffle (51), or on the exchanger shell (54), among other possible components. A repulsive charge on the tubes (55) is also useful. In the four pass design (FIG. 6), tube support baffles (61) are arranged in such a way as to direct fluid flow in four vertically configured compartments. The multiple compartments afford the ability to increase fluid velocity along the tubes while maintaining heat transfer efficiency, but this comes at the price of a larger pressure drop across the exchanger. These baffles are potential candidates for the charge application of this invention. Alternatively, the floating head (62) or the shell (63) are possible charge recipients.

Figure 7:
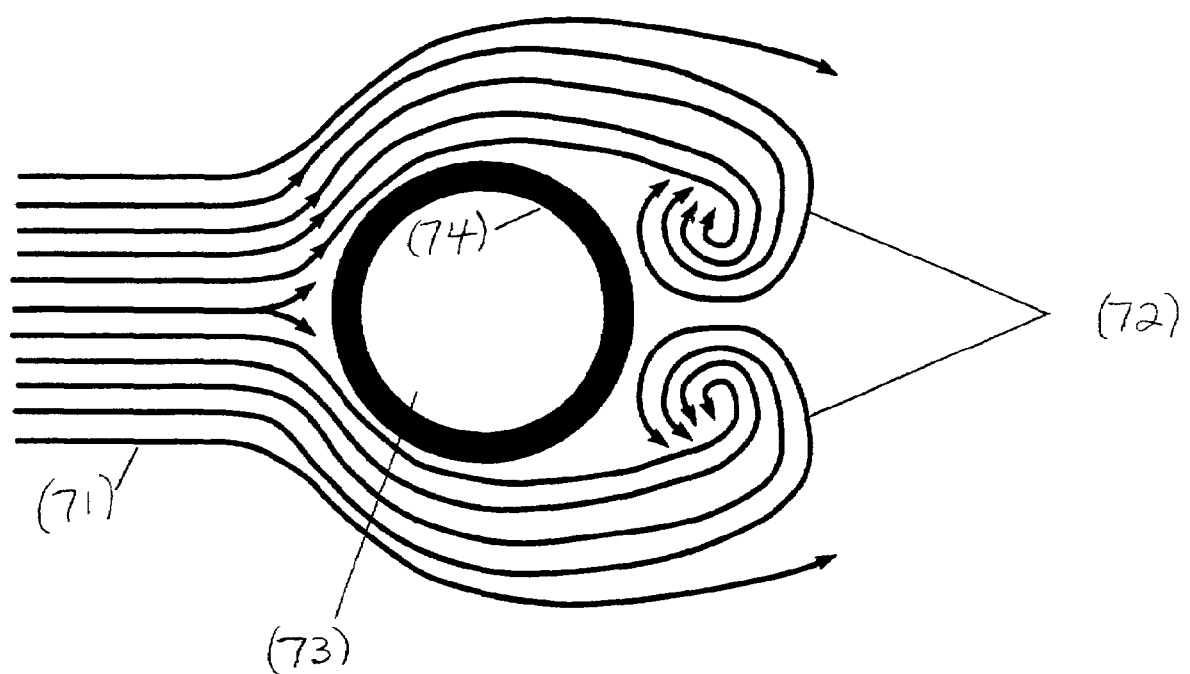
FIG. 7: Direct perpendicular flow across a tube to create turbulence behind the tube. This turbulence promotes good heat transfer.

As we have discussed, in any design, the application of a repulsive charge on the tubes is useful. These are the critical surfaces at which heat transfer occurs. The flow of the hot CSO contacts the shell-side surface of the tubes in a manner described as cross-flow (FIG. 7). This flow pattern (71) creates a vortex (72) behind the tube (73) which promotes good heat transfer. Over time, fouling develops on the surface of these tubes causing heat transfer efficiency to decline. As this proceeds, the fouling will increase to a point where the equipment must be taken off-line and cleaned. Applying the electric charge to tube wall (74) of the heat exchanger will prevent or significantly reduce the frequency of maintenance.

Alternatively, the electric charge may be applied at some point upstream of the heat exchangers. For example, the charge could be applied to the slurry settler (FIG. 8). The slurry settler (81) is an apparatus which employs gravity settling to clarify slurry oil product. Main column bottoms (82) feed the settler. Clarified Oil Product (83) is taken from the top while the slurry settler bottoms (84) are sent back to the reactor riser. By judiciously applying the charge to the slurry settler, enhanced separation of contaminants (85) may be realized by combining the gravitational settling with the use of an applied electric charge to trap the contaminants and keep them clear of the critical process elements. One particularly useful area in which to apply the voltage is on the conical section of the slurry settler. This would promote enhanced concentration of the contaminant in the settler bottoms. This is an example of an alternative embodiment in which the electric charge is placed on a process component other than the heat exchanger.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. A method for the reduction of fouling of process components within a liquid hydrocarbon stream comprising the steps of:

applying an electric charge to an object within a flow path of said liquid hydrocarbon stream for more than 5 minutes, wherein said liquid hydrocarbon stream contains at least one contaminant;

flowing said liquid hydrocarbon stream past said electric charge; and then adjusting the magnitude of said electric charge while continuing said flowing step.

2. The method according to claim 1, wherein said object is a heat exchanger.

3. The method according to claim 2, wherein said step of applying the electric charge comprises applying an electric charge to the chassis or shell of said heat exchanger.

4. The method of claim 1, further comprising determining a level of contaminants in the liquid hydrocarbon stream.

5. The method of claim 4 wherein said step of determining a level of contaminants utilizes measurement of the turbidity of the fluid stream or an analytical measurement indicative of contaminant concentration of the liquid hydrocarbon stream.

6. A method for improved hydrocarbon refining efficiency comprising the steps of:

catalytically cracking a liquid hydrocarbon mixture to produce an output mixture enhanced in low molecular weight liquid hydrocarbons relative to said hydrocarbon mixture;

separating by distillation said output mixture into petroleum fractions;

drawing a liquid hydrocarbon stream from said petroleum fractions;

flowing said liquid hydrocarbon stream through a heat exchanger;

repeating said step of separating or said steps of catalytically cracking and separating on said liquid hydrocarbon stream;

applying an electric charge to an object within a flow path of said liquid hydrocarbon stream for more than 5 minutes;

flowing said liquid hydrocarbon stream past said electric charge; and adjusting the magnitude of said electric charge while continuing said flowing step.

7. A method for the prevention of process component fouling within a liquid hydrocarbon stream, comprising the steps of:

initiating an electric charge to one or more process components for contacting a liquid hydrocarbon stream, wherein said liquid hydrocarbon stream contains at least one contaminant;

initiating a flow of the liquid hydrocarbon stream past the electric charge and the one or more process components;

applying the electric charge to the flowing liquid hydrocarbon stream for more than 5 minutes; and then adjusting the electric charge as the liquid hydrocarbon stream flows in fluid communication with the one or more process components.

8. The method according to claim 7, wherein the one or more process components comprises a heat exchanger.

9. The method according to claim 8, wherein the electric charge is applied to a chassis or shell of said heat exchanger.

10. A method for processing a liquid hydrocarbon process stream, comprising:

initiating a process run of a liquid hydrocarbon process stream through one or more process components adapted to exchange heat with the liquid hydrocarbon process stream;

initiating an electric charge to at least one of the one or more process components;

flowing the liquid hydrocarbon process stream in fluid communication with the at least one of the one or more process components having the electric charge applied thereto;

continually applying the electric charge to the at least one of the one or more process components during the process run while the liquid hydrocarbon process stream is in fluid communication therewith; and adjusting the electric charge to the at least one of the one or more process components during the process run.

11. The method according to claim 10, wherein the one or more process components comprises a heat exchanger.

12. The method according to claim 11, wherein the electric charge is applied to a chassis of said heat exchanger.

13. The method according to claim 11, wherein the electric charge is applied to a shell of said heat exchanger.

14. The method according to claim 11, wherein adjusting the electric charge to the at least one of the one or more process components during the process run comprises adjusting the electric charge to the shell of the heat exchanger.

* * * * *